United States Patent
Yano (10) Patent No.: US 10,806,682 B2
(45) Date of Patent: Oct. 20, 2020

(54) COSMETIC PRODUCT

(71) Applicant: TOKIWA CORPORATION, Nakatsugawa-shi, Gifu (JP)

(72) Inventor: Hidekazu Yano, Kawaguchi (JP)

( * ) Notice: Subject to any disclaimer, the term of this patent is extended or adjusted under 35 U.S.C. 154(b) by 0 days.

(21) Appl. No.: 16/167,177

(22) Filed: Oct. 22, 2018

(65) Prior Publication Data

US 2019/0125633 A1 May 2, 2019

(30) Foreign Application Priority Data

Nov. 2, 2017 (JP) ................................ 2017-212820

(51) Int. Cl.
| | |
|---|---|
| *A61K 8/02* | (2006.01) |
| *A45D 40/26* | (2006.01) |
| *A61Q 1/10* | (2006.01) |
| *A61K 8/31* | (2006.01) |
| *A61K 8/92* | (2006.01) |
| *A61K 8/25* | (2006.01) |
| *A61K 8/26* | (2006.01) |
| *A61K 8/29* | (2006.01) |

(52) U.S. Cl.
CPC .......... *A61K 8/0216* (2013.01); *A45D 40/265* (2013.01); *A61K 8/25* (2013.01); *A61K 8/26* (2013.01); *A61K 8/29* (2013.01); *A61K 8/31* (2013.01); *A61K 8/922* (2013.01); *A61Q 1/10* (2013.01); *A45D 2200/051* (2013.01); *A45D 2200/1009* (2013.01); *A61K 2800/26* (2013.01); *A61K 2800/436* (2013.01); *A61K 2800/48* (2013.01); *A61K 2800/87* (2013.01)

(58) Field of Classification Search
CPC ................................ A61Q 1/10; A45D 40/265
See application file for complete search history.

(56) References Cited

U.S. PATENT DOCUMENTS

| | | | | |
|---|---|---|---|---|
| 4,828,419 | A * | 5/1989 | Porter ................... | A45D 33/00 132/317 |
| 5,332,325 | A * | 7/1994 | Crosnier .............. | A45D 34/043 401/119 |
| 2006/0222615 | A1* | 10/2006 | Kuroda ................. | A61K 8/585 424/70.12 |
| 2007/0175788 | A1* | 8/2007 | Holba .................... | A45D 40/00 206/471 |
| 2015/0218381 | A1* | 8/2015 | O'Halloran ............ | C09C 1/021 556/466 |
| 2015/0257996 | A1* | 9/2015 | Howell .................... | A61K 8/42 424/401 |
| 2019/0216711 | A1* | 7/2019 | Fujii ........................ | A61K 8/19 |

FOREIGN PATENT DOCUMENTS

| | | |
|---|---|---|
| JP | 2011-079767 | 4/2011 |
| JP | 2012077049 A * | 4/2012 |

* cited by examiner

*Primary Examiner* — Gina C Justice
(74) *Attorney, Agent, or Firm* — Soei Patent & Law Firm (57) ABSTRACT

A cosmetic product includes a container main body that has an opening at one end thereof and contains a cosmetic therein, and a lid that has an application tool provided with an application element at a tip portion thereof and inserted into the opening part. When the lid is attached to the container main body, the application element and the cosmetic are brought into contact with each other and the cosmetic is hermetically sealed. The cosmetic contains (A) wax which is solid at 25° C., (B) powder, (C) film-forming agent, and (D) volatile oil agent, and a content of the (C) film-forming agent is 10% to 40% by mass based on a total amount of the cosmetic.

14 Claims, 1 Drawing Sheet

COSMETIC PRODUCT

CROSS-REFERENCE TO RELATED APPLICATIONS

This application claims the benefit of priority from Japanese Patent Application No. 2017-212820, filed on Nov. 2, 2017, the entire contents of which are incorporated herein by reference.

TECHNICAL FIELD

The present invention relates to a cosmetic product.

BACKGROUND

An oily solid cosmetic is composed mainly of a solid oil such as wax, a powder, and a liquid oil, and is manufactured to include basic properties such as filling moldability, usability (e.g., smooth application on the skin), and other performance characteristics of a cosmetic film such as persistence of the makeup.

The container forms of cosmetic products are diversified. For example, to achieve simplicity use and cost reduction, a container may be provided with an application tool such that a cosmetic tip, puff, or other type of application element is continuously in direct contact with a cosmetic. At the time of storage, the application element does not sink into the cosmetic and an oil ingredient of the cosmetic does not permeate into the application element. Additionally, at the time of use, an appropriate amount of the cosmetic is taken out by the application element and the cosmetic does not scatter as powder.

In Japanese Unexamined Patent Publication No. 2011-79767, it has been proposed to blend a lipophilic gelling agent such as dextrin fatty acid ester or inulin fatty acid ester in a cosmetic.

SUMMARY

The cosmetic described in Japanese Unexamined Patent Publication No. 2011-79767 has low hardness and thus does not satisfy usability since the application element tends to sink into the cosmetic, and the cosmetic adheres on a portion of the application element other than a portion that directly touches the skin, and the like.

In order to prevent the application element from sinking into the cosmetic, the hardness of the cosmetic may be increased. However, increasing the hardness of the cosmetic may affect the ability to take out an appropriate amount of the cosmetic with an application element, and the usability tends to be impaired. Therefore, the hardness of a cosmetic is adjusted so that filling moldability at the time of production and performances of a cosmetic film are not impaired.

Disclosed herein is a cosmetic product comprising a cosmetic which is filled in a container with sufficient filling moldability, and an application element which is in contact with the cosmetic. Additionally, the application element does not tend to sink into the cosmetic, and the cosmetic product is manufactured such that an appropriate amount of the cosmetic can be taken out at the time of use. Still further, a cosmetic film may be formed which has sufficient performance such as persistence of the makeup.

In some examples, the cosmetic product may comprise a container main body that has an opening at one end thereof and contains a cosmetic therein, and a lid that has an application tool provided with an application element at a tip portion thereof and inserted into the opening. When the lid is attached to the container main body, the application element and the cosmetic are brought into contact with each other and the cosmetic is hermetically sealed. Additionally, the cosmetic may comprise (A) wax which is solid at 25° C., (B) powder, (C) film-forming agent, and (D) volatile oil agent. In some examples, a content of the (C) film-forming agent is 10% to 40% by mass based on a total amount of the cosmetic.

In some examples cosmetic products, the cosmetic has sufficient filling moldability, the application element is difficult to sink into the cosmetic, an appropriate amount of the cosmetic can be taken out at the time of use, and a cosmetic film which has sufficient performances such as persistence of makeup can be formed. By applying the cosmetic having the above-mentioned composition to a container in which the cosmetic is to be hermetically sealed, the (D) volatile oil agent may be blended in the cosmetic, so that even in a case where hardness of the cosmetic is increased by a combination of the (D) volatile oil agent, the (A) wax which is solid at 25° C., and a specific amount of the (C) film-forming agent, the desired properties of the cosmetic may be achieved. For example, the filling moldability, the taking-out of the cosmetic, and the performances of the cosmetic film can be achieved in a compatible manner with one another.

Additionally, the cosmetic film can be manufactured to achieve desired properties such as coloring property, quick-drying property, persistence of makeup, and transfer resistance.

In some examples, the (A) wax which is solid at 25° C. comprises a hydrocarbon-based wax and a vegetable-based wax. By combining the hydrocarbon-based wax and the vegetable-based wax, an appropriate amount of the cosmetic can be taken out at the time of use, and the application element is sufficiently prevented from sinking into contents at the time of storage.

In addition, in some examples, the (B) powder may comprise calcium carbonate and the cosmetic may be a cosmetic for eyes.

Furthermore, the (B) powder may comprise a glittering powder.

The glittering powder can give a gorgeous impression, a three-dimensional feeling, and a glossy feeling, and can be used, in particular, in cosmetics for point makeup. On the other hand, the glittering powder has a property of easily aggregating, and, when it is applied to the skin, the pearl shade may become uneven and reduce a sense of adhesiveness to the skin. On the other hand, when the glittering powder is blended, application unevenness is sufficiently suppressed, so that a cosmetic film having sufficient transfer resistance can be formed.

The cosmetic product may comprise a cosmetic which is filled in a predetermined container with sufficient filling moldability, and an application element which is in contact with the cosmetic. Additionally, the cosmetic product may include an application element which does not tend to sink into the cosmetic. Still further, the cosmetic product may be manufactured such that an appropriate amount of the cosmetic may be taken out at the time of use, and a cosmetic film has sufficient performance such as persistence of the makeup.

DETAILED DESCRIPTION

The cosmetic product may comprise a container main body that has an opening at one end thereof and that contains a cosmetic therein. Additionally, the cosmetic product may comprise a lid that has an application tool with an application element at a tip portion thereof and is inserted into the opening. In some examples, in which the lid is attached to the container main body, the application element and the cosmetic are brought into contact with each other and the cosmetic is hermetically sealed.

Figure 1A:
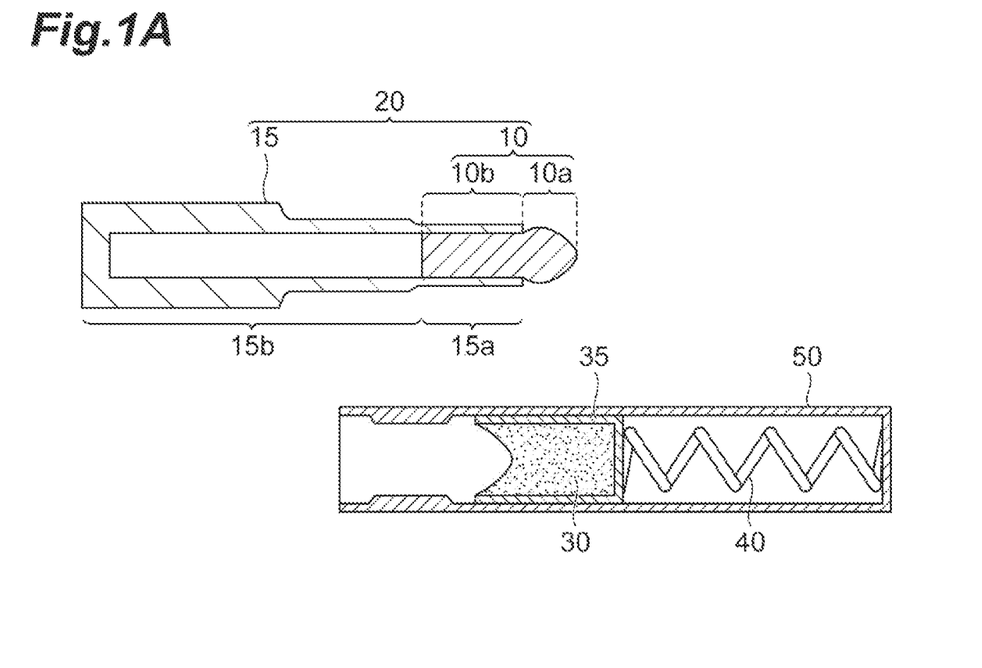
FIGS. 1A and 1B illustrate schematic cross-sectional views of an example cosmetic product.
Figure 1B:
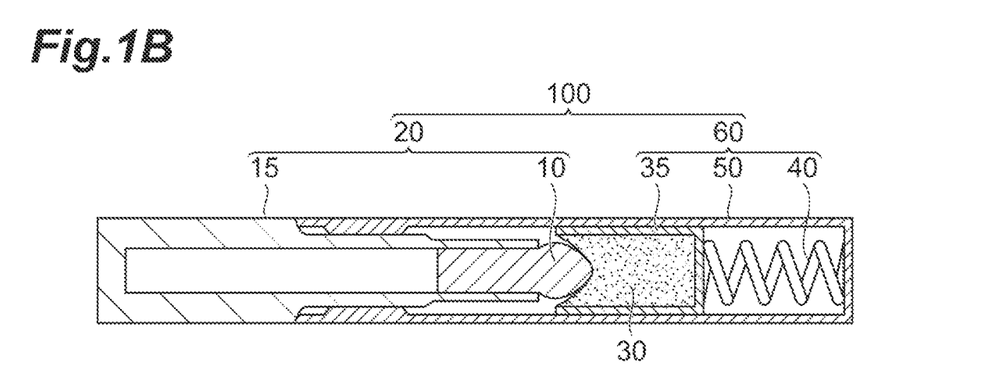

The example cosmetic product 100 illustrated in FIGS. 1A and 1B comprises a lid 20 configured to have an application tool 15 provided with an application element 10 at a tip portion. Additionally, the cosmetic product 100 comprises a container main body 50 that includes a cosmetic-containing part 35 in which a cosmetic 30 is contained and an elastic body 40 that can press the cosmetic-containing part 35 toward an opening. In the application tool 15 provided with the application element 10 at a tip portion thereof, the application element 10 is composed of a front end part 10a exposed from the application tool 15 and a rear end part 10b held by a tip portion 15a of the application tool 15. Additionally, the application tool 15 is composed of the tip portion 15a holding the rear end part 10b of the application element 10 and a rear end portion 15b.

FIG. 1B additionally illustrates an example configuration in which the lid 20 is attached to the container main body 50, the application element 10 and the cosmetic 30 come in contact with each other, and the cosmetic 30 is hermetically sealed by the lid 20. In some examples, a protrusion is provided on an inner wall surface of the container main body 50 in a circumferential direction, and the protrusion abuts against an outer wall surface of the application tool 15, so that the container main body 50 and the lid 20 are engaged with each other, and the cosmetic 30 is hermetically sealed.

The protrusion may be modified in position, number, and shape such that the container main body and the lid are engaged with each other and the cosmetic is hermetically sealed. In addition, coupling between the lid and the container main body can also be changed to screwing means.

A spring or the like may be used as the elastic body 40 that presses the containing part 35.

Examples of a material of the application element include a foamed plastic such as felt and urethane, an elastomer resin such as nitrile rubber, hair, and a synthetic fiber. The application element may be formed of a core material and an outer layer covering the core material. For example, the core material of the application element may comprise foamed plastic and the outer layer may comprise an elastomer resin and an application element obtained by securing a nylon fiber to an elastomer resin as the core material. The application element may comprise a porous material having good cosmetic-holding performance.

In some types of cosmetic products, when the application element is brought into contact with the skin and deformed, an attached cosmetic may lump and fall, or the cosmetic may adhere on an unnecessary location of the skin. The cosmetic may fall off when the cosmetic contains only wax as an oil ingredient.

The shape of the application element may be formed as a pen tip or brush tip shape of which a diameter gradually decreases toward its tip. However, other shapes also may be used. For example, depending on a cosmetic use such as eyeshadow or lipstick, the shape of the application element may be selected from a variety of shapes such as a spherical shape and a spatula shape.

In some examples, the container allows the application element and the cosmetic to be brought into contact with each other at the time of storage and allows the cosmetic to be hermetically sealed.

The cosmetic composition may comprise (A) wax which is solid at 25° C. (hereinafter also referred to as Ingredient (A) in some examples), (B) powder (hereinafter also referred to as Ingredient (B) in some examples), (C) film-forming agent (hereinafter also referred to as Ingredient (C) in some examples), and (D) volatile oil agent (hereinafter also referred to as Ingredient (D) in some examples).

<(A) Wax which is Solid at 25° C.>

Wax which is solid at 25° C. may include a hydrocarbon-based wax such as paraffin wax, microcrystalline wax, polyethylene wax, Fischer-Tropsch wax, ceresin, or ozokerite; a vegetable-based wax such as hardened castor oil, hydrogenated jojoba oil, candelilla wax, carnauba wax, or rice wax; and an animal-based wax such as beeswax or whale wax. In some examples, wax which is solid at 25° C. may include polyethylene wax, Fischer-Tropsch wax, candelilla wax, or carnauba wax.

For these waxes, one kind may be used alone, or two or more kinds may be used in combination.

A wax which is solid at 25° C. refers to a wax which does not flow when tilted at 25° C.

From the viewpoint of suppression of sinking of the application element and stability over time, the Ingredient (A) may comprise a hydrocarbon-based wax and a vegetable-based wax. For example, a blending ratio thereof, that is, [hydrocarbon-based wax]:[vegetable-based wax] may be 10:1 to 1:10, 9:1 to 1:9, or 7:3 to 3:7 in terms of mass ratio.

A content of the Ingredient (A) in the cosmetic may be 1% to 20% by mass, 1% to 15% by mass, or 2% to 12% by mass, based on the total amount of the cosmetic. In some applications of uses of the cosmetic, one or more properties of the cosmetic may be improved by providing an amount of the content at the smaller example range disclosed above, for example 2% to 12% by mass. When the content of the Ingredient (A) is within the above ranges, an appropriate amount of the cosmetic can be taken out at the time of use, and the application element can be made difficult to sink into contents at the time of storage.

<(B) Powder>

The powder may include an extender powder, a coloring pigment, and the like.

The extender powder may include an inorganic powder, a synthetic inorganic powder, an organic powder, a metal soap, a synthetic polymer powder, and the like. In some examples, the extender power may include mica, kaolin, sericite, talc, phlogopite, synthetic mica, silica, calcium carbonate, magnesium carbonate, aluminum oxide, boron nitride, zinc stearate, aluminum stearate, zinc myristate, a polyethylene powder, urethane beads, polymethyl methacrylate, an organopolysiloxane elastomer, and the like, or any combination thereof. A shape of the extender powder may comprise a spherical powder having an average particle diameter of 1 to 50 μm.

The coloring pigment may include red iron oxide, yellow iron oxide, black iron oxide, cobalt oxide, Ultramarine blue, Prussian blue, titanium oxide, zinc oxide, a pearl pigment (titanium mica, fish scale foil, bismuth oxychloride, and the like), an organic pigment (Red No. 228, Red No. 226, Blue No. 404, Red No. 202, Yellow No. 4 Aluminum Lake, and the like), a natural pigment (carmine, safflower, and the like), and the like, or any combination thereof.

From the viewpoint of adhesiveness to the skin at the time of application, the cosmetic may comprise calcium carbonate as the Ingredient (B). In this case, the cosmetic can be used as a cosmetic for eyes. Specific uses may include eyeshadow, eyeliner, eyebrow pencil, and mascara.

From the viewpoint of achieving both good adhesiveness to the skin and usability with less squeaky feeling, a content of calcium carbonate in the cosmetic may be 7.5 to 80 parts by mass, or 12 to 50 parts by mass, with respect to 100 parts by mass of a total of the Ingredient (B).

The cosmetic may further comprise a glittering powder as the Ingredient (B) in order to impart a pearl feeling to a cosmetic film.

The glittering powder may be obtained by coating a surface of a plate-like powder such as synthetic phlogopite, mica, glass, silica, and alumina with one or more coloring agents such as titanium oxide, iron oxide, silicon oxide, chromium oxide, chromium hydroxide, gold, silver, carmine, and an organic pigment, those obtained by cutting a film stock such as polyethylene terephthalate/polymethyl methacrylate laminate powder, polyethylene terephthalate/aluminum vapor-deposited powder, and polyethylene terephthalate/gold vapor-deposited laminate powder into a predetermined shape, and the like, or any combination thereof.

In some examples, the glittering powder may have an aspect ratio of 40 to 120. Additionally, the glittering powder may have a particle diameter (maximum diameter) of 3 to 120 μm.

The cosmetic may comprise an amount of the glittering powder having a content of 10% to 35% by mass, or 15% to 30% by mass, based on the total amount of the cosmetic. For the example cosmetic, even when the amount of glittering powder is contained in the above content, application unevenness is sufficiently suppressed, a cosmetic film having a sufficient transfer resistance can be formed, and a gorgeous impression, a three-dimensional feeling, and a glossy feeling can be imparted.

Ingredient (B) may be manufactured using various surface treatments such as a water repellent treatment and a water repellent/oil repellent treatment.

A content of the Ingredient (B) in the cosmetic may be 1% to 40% by mass, 10% to 35% by mass, or 15% to 30% by mass, based on the total amount of the cosmetic. In some applications of uses of the cosmetic, one or more properties of the cosmetic may be improved by providing an amount of the content at the smaller example range disclosed above, for example 15% to 30% by mass.

<(C) Film-Forming Agent>

The film-forming agent may include trimethylsiloxy silicic acid, an acrylic/silicone resin, or polyalkylsilsesquioxane, and the like, or any combination thereof.

Trimethylsiloxy silicic acid is a compound having a crosslinked structure with a siloxane structure as a main skeleton and is represented by the formula $[(CH_3—)_3 SiO_{1/2}]_x[SiO_2]_y$. Commercially available products of trimethylsiloxy silicic acid, in which a volatile oil agent or silicone oil is mixed, include BELSIL TMS803 (manufactured by Wacker Asahikasei Silicone Co., Ltd.), and KF-7312F, KF-7312J, KF-7312K, KF-7312T, X-21-5595 (manufactured by Shin-Etsu Chemical Co., Ltd.).

The acrylic/silicone resin is a polymer in which a functional group of an acrylic resin is modified with silicone. In some examples, the acrylic/silicone resin may include an (acrylates/polytrimethylsiloxy methacrylate) copolymer, an (alkyl acrylate/diacetone amide/amodimethicone) copolymer AMP, (alkyl acrylate/dimethicone) copolymer, an (acrylates/stearyl acrylate/dimethicone methacrylate) copolymer, and the like, or any combination thereof. Commercially available products of acrylic/silicone resin include KP-541, KP-543, KP-545, KP-549, KP-550, KP-575, KP-561P, KP-562P (manufactured by Shin-Etsu Chemical Co., Ltd.), and the like.

The polyalkylsilsesquioxane is a branched crosslinked form of an alkyl-modified silicone. The polyalkylsilsesquioxane may comprise polymethyl silsesquioxane, polypropyl silsesquioxane, and the like. Commercially available products of polyalkylsilsesquioxane include SilForm Flexible resin, SilForm Flexible fluid (manufactured by Momentive Performance Materials Co., Ltd.), 670 Fluid (manufactured by Dow Corning Toray Co., Ltd.), and the like.

From the viewpoint of persistence of makeup and transfer resistance, the Ingredient (C) may comprise trimethylsiloxy silicic acid.

In some examples, a content of the film-forming agent may be 10% to 40% by mass based on the total amount of the cosmetic. The content of the film-forming agent may be set to such a range to form a cosmetic film having a particular coloring property, persistence of makeup, and transfer resistance while maintaining the ability to remove the cosmetic out of the container and prevent the application element from sinking into the cosmetic.

Furthermore, from the viewpoint of persistence of makeup and transfer resistance, a content of the Ingredient (C) in the cosmetic may be 35% by mass, or 10% to 30% by mass, based on the total amount of the cosmetic.

<(D) Volatile Oil Agent>

In some examples, the volatile oil agent has a boiling point of 250° C. or lower at 1 atm (101.325 kPa).

The volatile oil agent may include a silicone-based oil agent such as methyl trimethicone, decamethyl tetrasiloxane, decamethyl cyclopentasiloxane, or octamethyl trisiloxane, and a hydrocarbon-based solvent such as isododecane and isoparaffin, and the like. Among these, from the viewpoint of persistence of makeup, quick-drying property, and stability over time, methyl trimethicone may be selected.

A content of the Ingredient (D) in the cosmetic may be 10% to 30% by mass, or 15% to 25% by mass, based on the total amount of the cosmetic. In some applications of uses of the cosmetic, one or more properties of the cosmetic may be improved by providing an amount of the content at the smaller example range disclosed above, for example 15% to 25% by mass.

The cosmetic may further comprise other oily ingredients other than the Ingredients (A) and (D). As the other oily ingredients, for example, a solid oil, a pasty oil, and a liquid oil used in cosmetic products can be used.

The solid oil may include esters such as glyceryl tribehenate and cholesterol fatty acid ester; higher fatty acids such as stearic acid, behenic acid, and 12-hydroxystearic acid; higher alcohols such as stearyl alcohol and behenyl alcohol; silicones such as alkyl-modified silicone and acrylic-modified silicone; sugar fatty acid esters such as dextrin palmitate and inulin stearate; and metal soaps such as magnesium stearate and aluminum stearate, or any combination thereof.

The pasty oil may include vaseline, dipentaerythrityl hexa(hydroxy stearate/stearate/rosinate), dipentaerythrityl tetra(hydroxy stearate/isostearate), dipentaerythrityl pentaisostearate, dipentaerythrityl hexahydroxystearate, glyceryl tri(caprylate/caprate/myristate/stearate), hydrogenated castor oil isostearate, phytosteryl oleate, sucrose hexa(oleate/palmitate/stearate), dimer dilinoleyl bis(behenyl/isostearyl/phytosteryl) dimer dilinoleate, (phytosteryl/isostearyl/cetyl/stearyl/behenyl) dimer dilinoleate, hydrogenated castor oil dimer dilinoleate, macadamia nut fatty acid phytosteryl, and bisdiglyceryl polyacyl adipate-2, or any combination thereof.

The liquid oil may include ester oils such as cetyl ethylhexanoate, ethylhexyl palmitate, triethyl hexanoin, isotridecyl isononanoate, isostearyl isostearate, neopentyl glycol diethylhexanoate, glyceryl tri(caprylic/caprate), neopentyl glycol dicaprate, propanediol diisostearate, trimethylolpropane triethylhexanoate, octyldodecyl myristate, octyldodecyl stearoyloxy stearate, diisostearyl malate, polyglyceryl triisostearate, dipentaerythrityl pentaisostearate, and trimethylolpropane triisostearate; silicone oils such as dimethicone and methylphenyl polysiloxane; hydrocarbon oils such as liquid paraffin, squalane, and olefin oligomer, vegetable oils such as sunflower seed oil, jojoba seed oil, castor oil and olive oil; higher fatty acids such as isostearic acid; higher alcohols such as isostearyl alcohol, octyldodecanol, and oleyl alcohol; hydrocarbon oils such as liquid paraffin, squalane, and hydrogenated polyisobutene, ester oil such as diisostearyl malate, polyglyceryl triisostearate, dipentaerythrityl pentaisostearate, and trimethylolpropane triisostearate, or any combination thereof.

In some examples, from the viewpoint of persistence of makeup and transfer resistance, the cosmetic may comprise the pasty oil. The above pasty oil may include dipentaerythrityl hexa(hydroxystearate/stearate/rosinate), dipentaerythrityl tetra(hydroxystearate/isostearate), dipentaerythrityl pentaisostearate, dipentaerythrityl hexahydroxystearate, dimer dilinoleyl bis(behenyl/isostearyl/phytosteryl) dimer dilinoleate, (phytosteryl/isostearyl/cetyl/stearyl/behenyl) dimer dilinoleate, macadamia nut fatty acid phytosteryl, and bisdiglyceryl polyacyl adipate-2, or any combination thereof.

The cosmetic may include one or more other ingredients used in cosmetic products such as a humectant, a surfactant, an ultraviolet absorber, an antiseptic, vitamins, a cosmetic ingredient, an antioxidant, and a fragrance can be blended to the above-mentioned ingredients.

In some examples, the hardness may be 0.05 to 2.0 N, and in other examples 0.1 to 1.0 N. In some applications of uses of the cosmetic, one or more properties of the cosmetic may be improved by providing a hardness at the smaller example range disclosed above, namely 0.1 to 1.0 N. The hardness of the cosmetic may be measured by the following procedure. First, a screw cup having a capacity of 30 mL is filled with a cosmetic which has been melted by heating, and a measurement sample which has been left to stand at 25° C. overnight is prepared. With respect to this measurement sample, hardness is measured using a FUDOH rheometer RT-2002D/D (manufactured by Rheotech Co., Ltd.) with a pressure sensitive shaft of 1 φ, a rate of needle insertion of 6 cm/min, and a depth of needle insertion of 10 mm.

Uses of the cosmetic product include a cosmetic for makeup such as lipstick, foundation, blusher, concealer, eyeshadow, eyeliner, eyebrow pencil, mascara, makeup base, or hair color, and a cosmetic for topcoat. Among these, eyeshadow, eyeliner, and eyebrow pencil are suitable also in view of a shape of the application element.

A method for producing a cosmetic product or obtaining a cosmetic bulk may comprise mixing the Ingredient (A), the Ingredient (B), the Ingredient (C), and the Ingredient (D) as described above, and, in some examples, other ingredients may be combined to fill a cosmetic-containing part, and then the mixture is solidified.

The cosmetic bulk may comprise the volatile oil agent (D) in order to have a sufficient filling property. In some examples, an adjustment to a content of the volatile oil agent in the cosmetic bulk and to a drying condition may be made at the time of solidification, so that the content of the Ingredient (D) in the cosmetic after filling and solidification is within the above-mentioned ranges. In some examples, the volatile oil agent used for the adjustment may include a silicone-based oil agent such as methyl trimethicone, decamethyl tetrasiloxane, decamethyl cyclopentasiloxane, or octamethyl trisiloxane, or a hydrocarbon-based solvent such as isododecane or isoparaffin, or any combination thereof.

ADDITIONAL EXAMPLES

Hereinafter, more details of cosmetic products are described with reference to additional examples.

Prior to the description of the examples, an evaluation method employed in each example will be described.

<Preparation of Evaluation Container>

An evaluation container having the same configuration as the container main body and the lid as shown in FIGS. 1A and 1B was prepared.

<Evaluation Method>

(Hardness)

A cosmetic which had been melted by heating was caused to fill a screw cup having a capacity of 30 mL, and left to stand at 25° C. overnight to prepare a measurement sample. With respect to this measurement sample, hardness was measured using a FUDOH rheometer RT-2002D/D (manufactured by Rheotech Co., Ltd.) with a pressure sensitive shaft of 1 φ, a rate of needle insertion of 6 cm/min, and a depth of needle insertion of 10 mm. Evaluation can be made as follows: the hardness is good if it is 0.10 N to 1.00 N; the hardness is moderate if it is equal to or greater than 0.05 N and less than 0.10 N, or greater than 1.00 N and equal to or less than 2.00 N; and the hardness is insufficient or too high if it is less than 0.05 N or greater than 2.00 N, or it is not measurable.

(Filling Moldability)

A cosmetic after defoaming was poured into a container main body of the evaluation container to perform filling, and evaluation was visually made on a filled state upon cooling and solidification according to the following criteria.

A: Good

B: Pattern-like filling unevenness is observed

C: Filling unevenness with gaps is observed

D: Filling cannot be done (Sinking of Application Element)

A cosmetic after defoaming was poured into a container main body of the evaluation container to perform filling, and cooled and solidified. An operation was repeated 20 times, in which a lid having an application tool provided with a cosmetic application element at a tip portion thereof was attached so that the cosmetic and the cosmetic application element were brought into contact with each other. Then, evaluation was visually made on sinking of the cosmetic application element according to the following criteria.

A: Sinking of the application element into the cosmetic occurs within a range of less than 70% of the tip front part (10a in FIG. 1A)

B: Sinking of the application element into the cosmetic occurs within a range of 70% to 100% of the tip front part (10a in FIG. 1A)

C: Sinking occurs up to a range of less than 20% of the tip portion (15a in FIG. 1A) of the application tool D: Sinking occurs up to a range of equal to or greater than 20% of the tip portion (15a in FIG. 1A) of the application tool (Taking-Out of Cosmetic)

A cosmetic after defoaming was poured into a container main body of the evaluation container to perform filling, and cooled and solidified. A lid having an application tool provided with an application element at a tip portion thereof was attached to the container main body, and a cosmetic product was prepared. With respect to this cosmetic product, a usability test was performed by a panel of ten experts, and evaluation was made on taking-out of the cosmetic onto the application element according to the following criteria.

(Evaluation Criteria)

A: The cosmetic is moderately taken out and is determined to be good by equal to or greater than 8 out of 10 people.

B: The cosmetic is moderately taken out and is determined to be good by 5 to 7 out of 10 people.

C: The cosmetic is moderately taken out and is determined to be good by 2 to 4 out of 10 people.

D: The cosmetic is moderately taken out and is determined to be good by 0 to 1 out of 10 people.

(Evaluation of Cosmetic Film)

A cosmetic after defoaming was poured into a container main body of the evaluation container to perform filling, and cooled and solidified. A lid having an application tool provided with an application element at a tip portion thereof was attached to the container main body, and a cosmetic product was prepared. With respect to this cosmetic product, a usability test was performed by a panel of ten experts, and evaluation was made on each evaluation item of goodness of coloring, quick-drying property, and persistence of makeup according to the following criteria.

(Evaluation Criteria)

A: Determined to be good by equal to or greater than 8 out of 10 people.

B: Determined to be good by 5 to 7 out of 10 people.

C: Determined to be good by 2 to 4 out of 10 people.

D: Determined to be good by 0 to 1 out of 10 people.

(Transfer Resistance)

The cosmetic was uniformly applied to an area of 1 cm×3 cm on a bio skin plate (manufactured by Beaulax), and after 10 minutes, paper was pressed against an applied part. Transfer of the cosmetic was visually evaluated in accordance with the following four levels.

(Evaluation Criteria)

A: No transfer of the cosmetic on the paper is observed

B: Transfer of a trace amount of the cosmetic on the paper is observed

C: Transfer of a small amount of the cosmetic on the paper is observed

D: Equal to or greater than half of the applied cosmetic transfers on the paper

Examples 1 to 6, and Comparative Example 1

A cosmetic (eyeshadow) having each of compositions shown in Table 1 was prepared by heating and dissolving ingredients 1 to 9, adding ingredients 10 and 11 thereto, and mixing and stirring. Subsequently, the obtained cosmetic was defoamed, directly filled the container main body of the evaluation container, cooled, and molded.

Examples 7 to 13

A cosmetic (eyeshadow) having each of compositions shown in Table 2 was prepared by heating and dissolving ingredients 1 to 12, adding ingredients 13 and 14 thereto, and mixing and stirring. Subsequently, the obtained cosmetic was defoamed, directly filled the container main body of the evaluation container, cooled, and molded.

Examples 14 to 17, and Comparative Examples 2 to 4

A cosmetic having each of compositions shown in Table 3 was prepared by heating and dissolving ingredients 1 to 7, adding ingredients 8 to 10 thereto, and mixing and stirring. Subsequently, the obtained cosmetic was defoamed, directly filled the container main body of the evaluation container, cooled, and molded.

Examples 18 to 19, and Comparative Examples 5 to 7

A cosmetic having each of compositions shown in Table 4 was prepared by heating and dissolving ingredients 1 to 9, adding ingredients 10 to 15 thereto, and mixing and stirring. Subsequently, the obtained cosmetic was defoamed, directly filled the container main body of the evaluation container, cooled, and molded. Comparative Example 5 could not be uniformly mixed, and thus filling and evaluation were not carried out.

TABLE 1

| | | Example 1 | Example 2 | Example 3 | Example 4 |
|---|---|---|---|---|---|
| 1 | Polyethylene wax-1 | 7 | 5 | — | — |
| 2 | Polyethylene wax-2 | — | — | 10 | — |
| 3 | Polyethylene wax-3 | — | — | — | 5 |
| 4 | Candelilla wax | 3 | 5 | 5 | 5 |
| 5 | Titanium oxide-coated mica powder-1 | 25 | 25 | 25 | 25 |
| 6 | Dimer acid ester-1 | 5 | 5 | 5 | 5 |
| 7 | Titanium oxide | 0.1 | 0.1 | 0.1 | 0.1 |
| 8 | Dimethicone-treated synthetic mica | 14.85 | 4.85 | 4.85 | 4.85 |
| 9 | Tocopherol | 0.05 | 0.05 | 0.05 | 0.05 |
| 10 | Trimethylsiloxy silicic acid | 20 | 30 | 30 | 30 |
| 11 | Methyl trimethicone | 25 | 25 | 25 | 25 |
| Hardness (N) | | 0.72 | 0.21 | 0.22 | 0.14 |
| Filling moldability | | A | A | A | A |
| Sinking of application element | | A | A | B | B |
| Taking-out of comestic | | A | B | B | A |
| Goodness of coloring | | A | A | A | A |
| Quick-drying property | | A | B | B | A |
| Persistence of makeup | | A | A | A | A |
| Transfer resistance | | A | A | A | A |

| | | Example 5 | Example 6 | Comparative Example 1 |
|---|---|---|---|---|
| 1 | Polyethylene wax-1 | 1 | 10 | — |
| 2 | Polyethylene wax-2 | — | — | — |
| 3 | Polyethylene wax-3 | — | — | — |
| 4 | Candelilla wax | 1 | 10 | — |
| 5 | Titanium oxide-coated mica powder-1 | 25 | 25 | 25 |
| 6 | Dimer acid ester-1 | 5 | 5 | 5 |
| 7 | Titanium oxide | 0.1 | 0.1 | 0.1 |
| 8 | Dimethicone-treated synthetic mica | 17.85 | 4.85 | 14.85 |
| 9 | Tocopherol | 0.05 | 0.05 | 0.05 |
| 10 | Trimethylsiloxy silicic acid | 20 | 20 | 20 |
| 11 | Methyl trimetihicone | 30 | 25 | 35 |
| Hardness (N) | | 0.11 | 1.8 | — |
| Filling moldability | | C | A | A |
| Sinking of application element | | A | A | D |
| Taking-out of comestic | | A | C | A |
| Goodness of coloring | | A | C | A |
| Quick-drying property | | B | A | A |

TABLE 1-continued

| | | | |
|---|---|---|---|
| Persistence of makeup | A | A | A |
| Transfer resistance | A | A | A |

TABLE 2

| | | Example 7 | Example 8 | Example 9 | Example 10 |
|---|---|---|---|---|---|
| 1 | Polyethylene wax-1 | 5 | 5 | 5 | 5 |
| 2 | Candelilla wax | 5 | 5 | 5 | 5 |
| 3 | Titanium oxide-coated mica powder-1 | 10 | 40 | — | — |
| 4 | Titanium oxide-coated mica powder-2 | — | — | 25 | — |
| 5 | Titanium oxide-coated mica powder-3 | — | — | — | 25 |
| 6 | Titanium oxide-coated mica powder-4 | — | — | — | — |
| 7 | Titanium oxide-coated mica powder-5 | — | — | — | — |
| 8 | Titanium oxide-coated mica powder-6 | — | — | — | — |
| 9 | Dimer acid ester-1 | 5 | 4.85 | 5 | 5 |
| 10 | Titanium oxide | 0.1 | 0.1 | 0.1 | 0.1 |
| 11 | Dimethicone-treated synthetic mica | 29.85 | — | 14.85 | 14.85 |
| 12 | Tocopherol | 0.05 | 0.05 | 0.05 | 0.05 |
| 13 | Trimethylsiloxy silicic acid | 20 | 20 | 20 | 20 |
| 14 | Methyl trimethicone | 25 | 25 | 25 | 25 |
| Hardness (N) | | 0.72 | 0.82 | 0.48 | 0.66 |
| Filling moldability | | A | B | A | A |
| Sinking of application element | | B | A | B | B |
| Taking-out of comestic | | A | A | B | A |
| Goodness of coloring | | A | A | A | A |
| Quick-drying property | | A | A | A | A |
| Persistence of makeup | | A | A | A | A |
| Transfer resistance | | A | A | A | A |

| | | Example 11 | Example 12 | Example 13 |
|---|---|---|---|---|
| 1 | Polyethylene wax-1 | 5 | 5 | 5 |
| 2 | Candelilla wax | 5 | 5 | 5 |
| 3 | Titanium oxide-coated mica powder-1 | — | — | — |
| 4 | Titanium oxide-coated mica powder-2 | — | — | — |
| 5 | Titanium oxide-coated mica powder-3 | — | — | — |
| 6 | Titanium oxide-coated mica powder-4 | 25 | — | — |
| 7 | Titanium oxide-coated mica powder-5 | — | 25 | — |
| 8 | Titanium oxide-coated mica powder-6 | — | — | 25 |
| 9 | Dimer acid ester-1 | 5 | 5 | 5 |
| 10 | Titanium oxide | 0.1 | 0.1 | 0.1 |
| 11 | Dimethicone-treated synthetic mica | 14.85 | 14.85 | 14.85 |
| 12 | Tocopherol | 0.05 | 0.05 | 0.05 |
| 13 | Trimethylsiloxy silicic acid | 20 | 20 | 20 |
| 14 | Methyl trimethicone | 25 | 25 | 25 |
| Hardness (N) | | 0.51 | 0.74 | 0.8 |
| Filling moldability | | A | A | C |
| Sinking of application element | | A | A | A |
| Taking-out of comestic | | A | A | B |
| Goodness of coloring | | A | A | A |
| Quick-drying property | | A | A | A |
| Persistence of makeup | | A | B | B |
| Transfer resistance | | A | B | B |

TABLE 3

| | | Example 14 | Example 15 | Example 16 | Example 17 |
|---|---|---|---|---|---|
| 1 | Polyethylene wax-1 | 5 | 5 | 5 | 5 |
| 2 | Candelilla wax | 5 | 5 | 5 | 5 |
| 3 | Titanium oxide-coated mica powder-1 | 25 | 25 | 25 | — |
| 4 | Dimer acid ester-1 | 5 | 5 | 5 | 5 |
| 5 | Titanium oxide | 0.1 | 0.1 | 0.1 | 0.1 |
| 6 | Dimethicone-treated synthetic mica | 9.85 | 19.85 | 15.85 | 9.85 |
| 7 | Tocopherol | 0.05 | 0.05 | 0.05 | 0.05 |
| 8 | Trimethylsiloxy silicic acid | 20 | 15 | 10 | 40 |
| 9 | Silicone acrylate | 5 | — | — | — |
| 10 | Methyl trimethicone | 25 | 25 | 34 | 35 |
| Hardness (N) | | 0.4 | 1.15 | 0.73 | 0.13 |
| Filling moldability | | A | B | A | A |
| Sinking of application element | | A | A | A | C |
| Taking-out of comestic | | A | A | B | C |
| Goodness of coloring | | A | A | A | C |
| Quick-drying property | | B | A | B | C |
| Persistence of makeup | | A | A | B | A |
| Transfer resistance | | A | A | B | A |

| | | Comparative Example 2 | Comparative Example 3 | Comparative Example 4 |
|---|---|---|---|---|
| 1 | Polyethylene wax-1 | 5 | 5 | 5 |
| 2 | Candelilla wax | 5 | 5 | 5 |
| 3 | Titanium oxide-coated mica powder-1 | 25 | 5.8 | 25 |
| 4 | Dimer acid ester-1 | 5 | 5 | 5 |
| 5 | Titanium oxide | 0.1 | 0.1 | 0.1 |
| 6 | Dimethicone-treated synthetic mica | 14.85 | 0.05 | 15.85 |
| 7 | Tocopherol | 0.05 | 0.05 | 0.05 |
| 8 | Trimethylsiloxy silicic acid | 1 | 45 | — |
| 9 | Silicone acrylate | — | — | — |
| 10 | Methyl trimethicone | 44 | 34 | 44 |
| Hardness (N) | | 0.84 | 0.1 | 0.3 |
| Filling moldability | | A | A | A |
| Sinking of application element | | A | D | A |
| Taking-out of comestic | | C | D | A |
| Goodness of coloring | | A | D | A |
| Quick-drying property | | C | D | D |
| Persistence of makeup | | D | D | D |
| Transfer resistance | | D | D | D |

TABLE 4

| | | Example 18 | Example 19 | Comparative Example 5 |
|---|---|---|---|---|
| 1 | Polyethylene wax-1 | 5 | 5 | 5 |
| 2 | Candelilla wax | 5 | 5 | 5 |
| 3 | Titanium oxide-coated mica powder-1 | 25 | 25 | — |
| 4 | Titanium oxide-coated mica powder-2 | — | — | 25 |
| 5 | Dimer acid ester-1 | 5 | 5 | 5 |
| 6 | Titanium oxide | 0.1 | 0.1 | 0.1 |
| 7 | Dimethicone-treated synthetic mica | 14.85 | 14.85 | 11.85 |
| 8 | Synthetic mica | — | — | 1 |
| 9 | Tocopherol | 0.05 | 0.05 | 0.05 |
| 10 | Trimethylsiloxy silicic acid | 20 | 20 | 27 |
| 11 | Decamethyl tetrasiloxane | 25 | — | — |
| 12 | Decamethyl cyclopentasiloxane | — | 25 | — |
| 13 | Methyl polysiloxane | — | — | — |
| 14 | Triethyl hexanoin | — | — | — |
| 15 | Diisostearyl malate | — | — | 20 |
| Hardness (N) | | 0.68 | 0.71 | — |
| Filling moldability | | B | B | |

TABLE 4-continued

| | | | |
|---|---|---|---|
| Sinking of application element | A | A | — |
| Taking-out of comestic | A | B | — |
| Goodness of coloring | A | A | — |
| Quick-drying property | A | B | — |
| Persistence of makeup | A | B | — |
| Transfer resistance | A | B | — |

| | | Comparative Example 6 | Comparative Example 7 |
|---|---|---|---|
| 1 | Polyethylene wax-1 | 5 | 5 |
| 2 | Candelilla wax | 5 | 5 |
| 3 | Titanium oxide-coated mica powder-1 | — | — |
| 4 | Titanium oxide-coated mica powder-2 | 25 | 25 |
| 5 | Dimer acid ester-1 | 5 | 5 |
| 6 | Titanium oxide | 0.1 | 0.1 |
| 7 | Dimethicone-treated synthetic mica | 9.85 | 9.85 |
| 8 | Synthetic mica | 1 | 1 |
| 9 | Tocopherol | 0.05 | 0.05 |
| 10 | Trimethylsiloxy silicic acid | 27 | 27 |
| 11 | Decamethyl tetrasiloxane | — | — |
| 12 | Decamethyl cyclopentasiloxane | — | — |
| 13 | Methyl polysiloxane | 22 | — |
| 14 | Triethyl hexanoin | — | 22 |
| 15 | Diisostearyl malate | — | — |
| Hardness (N) | | 0.38 | 0.96 |
| Filling moldability | | D | D |
| Sinking of application element | | C | C |
| Taking-out of comestic | | A | A |
| Goodness of coloring | | A | A |
| Quick-drying property | | D | D |
| Persistence of makeup | | D | D |
| Transfer resistance | | D | D |

In Tables 1 to 4, details of the respective ingredients are as follows.

Ingredient (A)

Polyethylene wax 1: "PERFORMALENE 400" (trade name, manufactured by BAKER HUGHES INC., weight average molecular weight of 400)

Polyethylene wax 2: "PERFORMALENE 500" (trade name, manufactured by BAKER HUGHES INC., weight average molecular weight of 500)

Polyethylene wax 3: "PERFORMALENE 655" (trade name, manufactured by BAKER HUGHES INC., weight average molecular weight 655)

Candelilla wax: "Purified candelilla wax refine" (trade name, manufactured by Watahan Trading Co., Ltd.)

Ingredient (B)

Titanium oxide-coated mica powder-1: "Timiron Starluster MP-115" (trade name, manufactured by Merck & Co., particle size of 18 to 25 μm)

Titanium oxide-coated mica powder-2: "Timiron Supersilk MP-1005" (trade name, manufactured by Merck & Co., particle size of 3.0 to 10 μm)

Titanium oxide-coated mica powder-3: "Timiron Silk" (trade name, manufactured by Merck & Co., particle size of 7 to 14 μm)

Titanium oxide-coated mica powder-4: "Timiron Splenid" (trade name, manufactured by Merck & Co., particle size of 18 to 25 μm)

Titanium oxide-coated mica powder-5: "Metashine 1080" (trade name, manufactured by Nippon Sheet Glass Co., Ltd., particle diameter of 75 to 100 μm)

Titanium oxide-coated mica powder-6: "Metashine 1120" (trade name, produced by Nippon Sheet Glass Co., Ltd., particle diameter of 105 to 135 μm)

Dimethicone-treated synthetic mica: "SA-PDM-10S" (trade name, manufactured by Miyoshi Kasei Co., Ltd.)

Synthetic mica: "PDM-10L" (trade name, manufactured by Topy Industries, Ltd.)

Ingredient (C)

Trimethylsiloxy silicic acid: "BELSIL TMS 803" (trade name, manufactured by Wacker Asahi Kasei Silicone Co., Ltd.)

Silicone acrylate: "KP-561" (trade name, manufactured by Shin-Etsu Chemical Co., Ltd.)

Ingredient (D)

Methyl trimethicone: "TMF-1.5" (trade name, manufactured by Shin-Etsu Chemical Co., Ltd.)

Decamethyltetrasiloxane: "KF-96L-1.5 cs" (trade name, manufactured by Shin-Etsu Chemical Co., Ltd.)

Decamethylcyclopentasiloxane: "KF-995" (trade name, manufactured by Shin-Etsu Chemical Co., Ltd.)

Other Ingredients

Dimer acid ester-1: "Plandool-G" (trade name, manufactured by Nippon Fine Chemical Co., Ltd., dimer dilinoleic acid dimer linoleyl bis(behenyl/isostearyl/phytosteryl))

Methyl polysiloxane: "KF-96A-6T" (trade name, manufactured by Shin-Etsu Chemical Co., Ltd.)

As shown in Tables 1 to 4, the cosmetic products obtained in Examples 1 to 19 were evaluated as "C", "B", or "A" for all of filling moldability, sinking of application element, taking-out of cosmetic, goodness of coloring, quick-drying property, persistence of makeup, and transfer resistance.

| | (Ingredient) | (Blending ratio (% by mass)) |
|---|---|---|
| 1. | Fischer-Tropsch wax *1 | 5.0 |
| 2. | Carnauba wax | 5.0 |
| 3. | Titanium oxide-coated mica powder-1 | 25.0 |
| 4. | Dimethicone-treated synthetic mica | 14.85 |
| 5. | Tocopherol | 0.05 |
| 6. | Dimer acid ester-1 | 5.0 |
| 7. | Titanium oxide | 0.1 |
| 8. | Trimethylsiloxy silicic acid | 20.0 |
| 9. | Methyl trimethicone | 25.0 |

Details of the above ingredientsare as follows.
*1: "CIREBELLE 108" (trade name, manufactured by Cirebelle (Pty) Ltd.)
Ingredients 3 to 9 are the same as those shown in Tables 1 to 4.

<Production Method>

Ingredients 1 to 7 were heated and dissolved, ingredients 8 and 9 were added thereto, and mixing and stirring was performed to prepare a cosmetic. Subsequently, the obtained cosmetic was defoamed, directly filled the container main body of the evaluation container, and cooled and molded to obtain an eyeshadow.

<Evaluation>

With respect to the obtained eyeshadow, the same evaluation as above was carried out. The results are shown in Table 5.

Example 21: Eyeshadow

| | (Ingredient) | (Blending ratio (% by mass)) |
|---|---|---|
| 1. | Polyethylene wax-1 | 3.0 |
| 2. | Candelilla wax | 7.0 |
| 3. | Titanium oxide-coated mica powder-1 | 25.0 |
| 4. | Dimethicone-treated synthetic mica | 14.85 |
| 5. | Tocopherol | 0.05 |

-continued

|   | (Ingredient) | (Blending ratio (% by mass)) |
|---|---|---|
| 6. | Dipentaerythrityl hexa(hydroxystearate/stearate/rosinate) *1 | 5.0 |
| 7. | Titanium oxide | 0.1 |
| 8. | Trimethylsiloxy silicic acid | 20.0 |
| 9. | Methyl trimethicone | 25.0 |

Details of the above ingredients are as follows.
*1: "COSMOL 168ARV" (trade name, manufactured by Nisshin OilliO Group, Ltd.)
Ingredients 1 to 5 and 7 to 9 are the same as those shown in Tables 1 to 4.

<Production Method>

Ingredients 1 to 7 were heated and dissolved, ingredients 8 and 9 were added thereto, and mixing and stirring was performed to prepare a cosmetic. Subsequently, the obtained cosmetic was defoamed, directly filled the container main body of the evaluation container, and cooled and molded to obtain an eyeshadow.

<Evaluation>

With respect to the obtained eyeshadow, the same evaluation as above was carried out. The results are shown in Table 5.

Example 22: Eyeshadow

|   | (Ingredient) | (Blending ratio (% by mass)) |
|---|---|---|
| 1. | Polyethylene wax-1 | 6.0 |
| 2. | Carnauba wax | 4.0 |
| 3. | Titanium oxide-coated mica powder-1 | 25.0 |
| 4. | Dimethicone-treated synthetic mica | 14.85 |
| 5. | Tocopherol | 0.05 |
| 6. | Dimer acid ester-1 | 5.0 |
| 7. | Titanium oxide | 0.1 |
| 8. | Trimethylsiloxy silicic acid | 20.0 |
| 9. | Methyl trimethicone | 25.0 |

The above ingredients 1 and 3 to 9 are the same as those shown in Tables 1 to 4.

<Production Method>

Ingredients 1 to 7 were heated and dissolved, ingredients 8 and 9 were added thereto, and mixing and stirring was performed to prepare a cosmetic. Subsequently, the obtained cosmetic was defoamed, directly filled the container main body of the evaluation container, and cooled and molded to obtain an eyeshadow.

<Evaluation>

With respect to the obtained eyeshadow, the same evaluation as above was carried out. The results are shown in Table 5.

Example 23: Eyeliner

|   | (Ingredient) | (Blending ratio (% by mass)) |
|---|---|---|
| 1. | Polyethylene wax-1 | 4.0 |
| 2. | Candelilla wax | 6.0 |
| 3. | Black iron oxide-coated mica titanium *1 | 4.0 |
| 4. | Light calcium carbonate | 5.0 |
| 5. | Tocopherol | 0.05 |
| 6. | Dipentaerythrityl pentaisostearate *2 | 11.0 |
| 7. | Ultramarine blue | 1.0 |
| 8. | Black iron oxide | 30.0 |
| 9. | Yellow iron oxide | 0.1 |

-continued

|   | (Ingredient) | (Blending ratio (% by mass)) |
|---|---|---|
| 10. | Red iron oxide | 0.1 |
| 11. | Titanium oxide | 0.1 |
| 12. | Trimethylsiloxy silicic acid *3 | 24.0 |
| 13. | Methyl trimethicone | 14.65 |

Details of the above ingredients are as follows.
*1: "Colorana Mica Black" (trade name, manufactured by Merck & Co.)
*2: "SALACOS DP-518N" (trade name, manufactured by Nisshin OilliO Group, Ltd.)
*3: "KF-7312T" (trade name, manufactured by Shin-Etsu Chemical Co., Ltd.)
Ingredients 1, 2, 5, 11 and 13 are the same as those shown in Tables 1 to 4.

<Production Method>

Ingredients 1 to 11 were heated and dissolved, ingredients 12 and 13 were added thereto, and mixing and stirring was performed to prepare a cosmetic. Subsequently, the obtained cosmetic was defoamed, directly filled the container main body of the evaluation container, and cooled and molded to obtain an eyeliner.

<Evaluation>

With respect to the obtained eyeliner, the same evaluation as above was carried out. The results are shown in Table 5.

Example 24: Lipstick

|   | (Ingredient) | (Blending ratio (% by mass)) |
|---|---|---|
| 1. | Polyethylene wax-1 | 4.0 |
| 2. | Candelilla wax | 4.0 |
| 3. | Dimethicone-treated synthetic mica | 32.7 |
| 4. | Tocopherol | 0.05 |
| 5. | Dipentaerythrityl pentaisostearate *1 | 11.0 |
| 6. | Blue 1 | 0.1 |
| 7. | Black iron oxide | 0.05 |
| 8. | Yellow iron oxide | 1.0 |
| 9. | Red iron oxide | 0.1 |
| 10. | Titanium oxide | 1.0 |
| 11. | Red 202 | 4.0 |
| 12. | Light calcium carbonate | 5.0 |
| 13. | Trimethylsiloxy silicic acid | 12.0 |
| 14. | Methyl trimethicone | 25.0 |

Details of the above ingredients are as follows.
*1: "SALACOS DP-518N" (trade name, manufactured by Nisshin OilliO Group, Ltd.)
Ingredients 1 to 4, 10, 13, and 14 are the same as those shown in Tables 1 to 4.

<Production Method>

Ingredients 1 to 12 were heated and dissolved, ingredients 13 and 14 were added thereto, and mixing and stirring was performed to prepare a cosmetic. Subsequently, the obtained cosmetic was defoamed, directly filled the container main body of the evaluation container, and cooled and molded to obtain a lipstick.

<Evaluation>

With respect to the obtained lipstick, the same evaluation as above was carried out. The results are shown in Table 5.

Example 25: Concealer

|   | (Ingredient) | (Blending ratio (% by mass)) |
|---|---|---|
| 1. | Polyethylene wax-1 | 4.0 |
| 2. | Candelilla wax | 6.0 |
| 3. | Dimethicone-treated synthetic mica | 0.7 |
| 4. | Tocopherol | 0.05 |

-continued

| | (Ingredient) | (Blending ratio (% by mass)) |
|---|---|---|
| 5. | Dipentaerythrityl pentaisostearate *1 | 11.0 |
| 6. | Black iron oxide | 0.05 |
| 7. | Yellow iron oxide | 2.0 |
| 8. | Red iron oxide | 0.3 |
| 9. | Titanium oxide | 24.9 |
| 10. | Light calcium carbonate | 5.0 |
| 11. | Trimethylsiloxy silicic acid | 23.0 |
| 12. | Methyl trimethicone | 23.0 |

Details of the above ingredients are as follows.
*1: "SALACOS DP-518N" (trade name, manufactured by Nisshin OilliO Group, Ltd.)
Ingredients 1 to 4, 9, 11, and 12 are the same as those shown in Tables 1 to 4.

<Production Method>

Ingredients 1 to 10 were heated and dissolved, ingredients 11 and 12 were added thereto, and mixing and stirring was performed to prepare a cosmetic. Subsequently, the obtained cosmetic was defoamed, directly filled the container main body of the evaluation container, and cooled and molded to obtain a concealer.

<Evaluation>

With respect to the obtained concealer, the same evaluation as above was carried out. The results are shown in Table 5.

Example 26: Eyebrow Pencil

| | (Ingredient) | (Blending ratio (% by mass)) |
|---|---|---|
| 1. | Polyethylene wax-1 | 3.0 |
| 2. | Candelilla wax | 2.0 |
| 3. | Dimethicone-treated synthetic mica | 22.35 |
| 4. | Tocopherol | 0.05 |
| 5. | Dipentaerythrityl pentaisostearate *1 | 11.0 |
| 6. | Black iron oxide | 2.2 |
| 7. | Yellow iron oxide | 2.1 |
| 8. | Red iron oxide | 1.6 |
| 9. | Titanium oxide | 4.7 |
| 10. | Light calcium carbonate | 5.0 |
| 11. | Trimethylsiloxy silicic acid | 23.0 |
| 12. | Methyl trimethicone | 23.0 |

Details of the above ingredients are as follows.
*1: "SALACOS DP-518N" (trade name, manufactured by Nisshin OilliO Group, Ltd.)
Ingredients 1 to 4, 9, 11, and 12 are the same as those shown in Tables 1 to 4.

<Production Method>

Ingredients 1 to 10 were heated and dissolved, ingredients 11 and 12 were added thereto, and mixing and stirring was performed to prepare a cosmetic. Subsequently, the obtained cosmetic was defoamed, directly filled the container main body of the evaluation container, and cooled and molded to obtain an eyebrow pencil.

<Evaluation>

With respect to the obtained eyebrow pencil, the same evaluation as above was carried out. The results are shown in Table 5.

TABLE 5

| | Example 20 | Example 21 | Example 22 | Example 23 |
|---|---|---|---|---|
| Hardness (N) | 0.84 | 0.82 | 0.82 | 0.46 |
| Filling moldability | B | B | B | A |
| Sinking of application element | B | A | A | B |
| Taking-out of comestic | B | A | A | A |
| Goodness of coloring | A | A | A | A |
| Quick-drying property | A | A | A | A |
| Persistence of makeup | A | A | A | A |
| Transfer resistance | A | A | A | A |

| | Example 24 | Example 25 | Example 26 |
|---|---|---|---|
| Hardness (N) | 1.26 | 0.52 | 0.45 |
| Filling moldability | A | A | A |
| Sinking of application element | A | B | A |
| Taking-out of comestic | A | A | A |
| Goodness of coloring | A | A | A |
| Quick-drying property | A | A | A |
| Persistence of makeup | A | A | A |
| Transfer resistance | A | A | A |

As shown in Table 5, the cosmetic products obtained in Examples 20 to 26 were evaluated as B or A for all of filling moldability, sinking of application element, taking-out of cosmetic, goodness of coloring, quick-drying property, persistence of makeup, and transfer resistance.

It is to be understood that not all aspects, advantages and features described herein may necessarily be achieved by, or included in, any one particular example embodiment. Indeed, having described and illustrated various examples herein, it should be apparent that other examples may be modified in arrangement and detail. We claim all modifications and variations coming within the spirit and scope of the subject matter claimed herein.

What is claimed is:

1. A cosmetic product comprising:
a solid cosmetic for eyes;
a container main body comprising:
an opening at one end thereof,
a cosmetic-containing part in which the solid cosmetic is contained, and
an elastic body configured to press the cosmetic-containing part toward the opening; and
a lid that has an application tool provided with an application element at a tip portion thereof and inserted into the opening,
wherein in a state where the lid is attached to the container main body, the application element and the solid cosmetic are brought into contact with each other by a pressing action of the elastic body and the solid cosmetic is hermetically sealed,
wherein the solid cosmetic comprises (A) wax which is solid at 25° C., (B) powder, (C) film-forming agent, (D) volatile oil agent and a pasty oil,
wherein the (A) wax which is solid at 25° C. comprises at least one hydrocarbon-based wax selected from the group consisting of polyethylene wax and Fischer-Tropsch wax, and at least one vegetable-based wax selected from the group consisting of candelilla wax and carnauba wax,
wherein the (B) powder comprises calcium carbonate and titanium oxide,
wherein a content of the (C) film-forming agent is 20% to 40% by mass based on a total amount of the solid cosmetic, and
wherein the pasty oil comprises at least one compound selected from the group consisting of dipentaerythrityl hexa(hydroxystearate/stearate/rosinate), dipentaerythrityl tetra(hydroxystearate/isostearate), dipentaerythrityl pentaisostearate, dipentaerythrityl hexahydroxystearate, dimer dilinoleyl bis(behenyl/isostearyl/phytosteryl) dimer dilinoleate, (phytosteryl/isostearyl/cetyl/stearyl/behenyl) dimer dilinoleate, macadamia nut fatty acid phytosteryl, and bisdiglyceryl polyacyl adipate-2.

2. The cosmetic product according to claim 1, wherein the (B) powder comprises a glittering powder.

3. The cosmetic product according to claim 1, wherein a mass ratio of hydrocarbon-based wax and vegetable-based wax ([hydrocarbon-based wax]:[vegetable-based wax]) is 10:1 to 1:10.

4. The cosmetic product according to claim 1, wherein a content of calcium carbonate is 7.5 to 80 parts by mass with respect to 100 parts by mass of a total of the (B) powder.

5. The cosmetic product according to claim 2, wherein a content of the glittering powder is 10% to 35% by mass based on the total amount of the solid cosmetic.

6. The cosmetic product according to claim 1, wherein the (C) film-forming agent comprises trimethylsiloxy silicic acid.

7. The cosmetic product according to claim 1, wherein the (D) volatile oil agent comprises methyl trimethicone.

8. The cosmetic product according to claim 1, wherein a content of the (A) wax which is solid at 25° C. is 1% to 20% by mass based on the total amount of the solid cosmetic.

9. The cosmetic product according to claim 1, wherein a content of the (B) powder is 1% to 40% by mass based on the total amount of the solid cosmetic.

10. The cosmetic product according to claim 1, wherein a content of the (D) volatile oil agent is 10% to 30% by mass based on the total amount of the solid cosmetic.

11. The cosmetic product according to claim 1, wherein a hardness of the solid cosmetic is 0.05 to 2.0 N.

12. The cosmetic product according to claim 1, wherein sinking of the application element into the solid cosmetic is suppressed at the time of storage.

13. The cosmetic product according to claim 1, wherein the application element comprises a porous material having a cosmetic-holding property.

14. The cosmetic product according to claim 1, wherein a content of the pasty oil is 4.85% to 11% by mass based on the total amount of the solid cosmetic.

* * * * *